United States Patent [19]

Cauwenbergh

[11] Patent Number: 5,476,852
[45] Date of Patent: Dec. 19, 1995

[54] METHOD OF TOPICALLY TREATING ACNE VULGARIS, HYPERKERATOTIC DERMATOSES, AND PHOTO-AGING OF THE SKIN

[75] Inventor: Gerard F. M. J. Cauwenbergh, Vorselaar, Belgium

[73] Assignee: Janssen Pharmaceutica N.V., Belgium

[21] Appl. No.: 111,094

[22] Filed: Aug. 24, 1993

Related U.S. Application Data

[63] Continuation of Ser. No. 540,544, Jun. 19, 1990, abandoned, which is a continuation-in-part of Ser. No. 510,636, Apr. 18, 1990, abandoned.

[30] Foreign Application Priority Data

May 3, 1989 [GB] United Kingdom .................. 8910069

[51] Int. Cl.$^6$ .................. A61K 34/495; A61K 31/20
[52] U.S. Cl. .................. 514/252; 514/559
[58] Field of Search .................. 514/252, 559

[56] References Cited

U.S. PATENT DOCUMENTS 4,888,342  12/1989  Kligman .................. 514/419

FOREIGN PATENT DOCUMENTS 0270316  6/1988  European Pat. Off. ..... A61K 31/415

OTHER PUBLICATIONS

Cox, *Chemical Abstract*, vol. 97, abstract No. 98378e, 1982.

*Primary Examiner*—Raymond Henley, III
*Assistant Examiner*—William R. A. Jarvis
*Attorney, Agent, or Firm*—Charles J. Metz

[57] ABSTRACT

A method of topically treating subjects suffering from acne, hyperkeratotic dermatoses and photo-aging of the skin, by administering to the skin of said subjects an effective amount of the antifungal compound ketoconazole and a retinoid is disclosed. Compositions comprising an inert carrier and as active ingredients the compound ketoconazole and a retinoid are described.

12 Claims, No Drawings

METHOD OF TOPICALLY TREATING ACNE VULGARIS, HYPERKERATOTIC DERMATOSES, AND PHOTO-AGING OF THE SKIN

CROSS-REFERENCE TO RELATED APPLICATION

This application is a continuation of application Ser. No. 07/540,544, filed Jun. 19, 1990, now abandoned, which in turn is a continuation-in-part of application Ser. No. 07/510,636, filed Apr. 18, 1990, now abandoned.

BACKGROUND OF THE INVENTION

Acne vulgaris has hitherto been treated primarily by topically applying keratolytic agents such as benzoylperoxide, antibacterial compounds, or combinations thereof such as, for example, benzoylperoxide and miconazole, said combination being described in U.S. Pat. No. 3,717,655.

In U.S. Pat. No. 3,729,568 the use of retinoids as topical anti-acne agents is described.

In Arch. Dermatol. 122, 629 (1986), Ghetti and al. report on the improvement in the acne of three women administered oral ketoconazole (300 mg b.i.d.) in the treatment of acne and hirsutism. Unfortunately, such massive daily doses of oral ketoconazole are not devoid of side effects and are potentially hepatotoxic. Further, in EP-0,207,316 there are described topical compositions comprising 1-substituted imidazoles and NSAIDs for treating acne.

Quite unexpectedly, it now has been found that ketoconazole alone and when administered topically can effectively be used in the treatment of humans suffering from dermatological conditions such as, for example, acne, hyperkeratotic dermatoses and photo-aging of the skin. Topical administration enhances both efficacy and safety of the drug.

DESCRIPTION OF THE INVENTION

The present invention is concerned with a method of topically treating subjects suffering from acne, in particular acne vulgaris, said method comprising the administration to the site of the acne on the skin of said subjects of an effective anti-acne amount of the compound ketoconazole.

Ketoconazole as mentioned hereinabove is the generic name of the compound (±)-cis-1-acetyl-4-[4-[[2-(2,4-dichlorophenyl)-2-(1H-imidazol-1-ylmethyl)-1,3-dioxolan-4-yl]methoxy]phenyl]piperazine, which may be represented by the formula

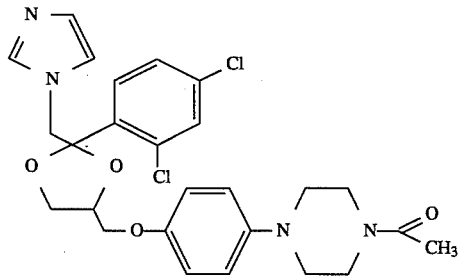

The compound ketoconazole used in the method of the present invention is a known antifungal agent and its preparation as well as its pharmacological properties are described in U.S. Pat. No. 4,335,125, incorporated herein by reference.

The compound ketoconazole can be used as such or in a pharmaceutically acceptable acid addition salt form, the latter being conveniently obtained by treating the base form with an appropriate acid. Appropriate acids comprise, for example, inorganic acids such as hydrohalic acids, e.g. hydrochloric or hydrobromic acid; sulfuric acid; nitric acid; phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. The term acid addition salt form as used hereinabove also comprises the solvates which the compound ketoconazole and its acid addition salts are able to form. Examples of such solvates are e.g. the hydrates, alcoholates and the like.

The term acne and more in particular acne vulgaris as used hereinabove is meant to comprise the chronic inflammation of the pilosebaceous system, i.e. the hair follicles and sebaceous glands of the skin, in particular the skin of the face, the back and the chest, Previous experience has indicated that the compound ketoconazole is an orally and topically active antifungal and antiandrogen agent while being a rather poor antibacterial agent, For example, the $ED_{50}$ value of ketoconazole against Salmonella spp. and Staphylococcus spp. was found to be well above 40 mg/kg bodyweight. Since acne is known to be associated with the bacterium *Propionibacterium acnes,* the present finding that ketoconazole—when applied topically—is effective in reducing or curing acne is surprising.

Further, it has been found that ketoconazole also may be used in a similar method of treating subjects suffering from hyperkeratotic dermatoses and skin diseases wherein the sebaceous glands are involved, such as rosacea. As examples of hyperkeratotic dermatoses there may be mentioned keratosis palmaris et plantaris, solar keratosis of extremities, callosities, Darier's disease, ichtyosis and lichen planus. Rosacea is chronic disease affecting the skin of the nose, forehead and cheeks marked by flushing, followed by red coloration due to dilatation of the capillaries with the appearance of papules and acne-like pustules. Administration of an effective amount of the compound ketoconazole, topically and/or systemically, to patients suffering from rosacea exerts a positive influence, in particular the acne-like pustules disappear and the papules are reduced in severity.

In still another aspect of the present invention, there is provided a method of topically treating subjects affected by photo-aging of the skin. The term photo-aging is meant to comprise the light-induced aging of skin exposed to sunlight, which is characterized by wrinkles, crow's feet and the like.

The compound ketoconazole used in the methods of the present invention is most preferably applied in the form of appropriate compositions, in particular compositions usually employed for the topical administration of drugs or cosmetic compositions. Said compositions constitute a further aspect of the present invention. Said compositions contain the active ingredient ketoconazole and a skin-acceptable carrier and may take a wide variety of forms such as, for example, solid forms, e.g. powders; liquid forms, e.g. solutions or suspensions in aqueous or oily mediums; or semi-liquid formulations, e.g. creams, gels, pastes, ointments, salves, tinctures.

Other such compositions are preparations of the cosmetic type, such as toilet waters, packs, lotions, skin milks or milky lotions. Said preparations contain, besides the active ingredient ketoconazole, components usually employed in such preparations. Examples of such components are oils, fats, waxes, surfactants, humectants, penetration enhancing agents, thickening agents, lipid absorbents, antioxidants, viscosity stabilizers, chelating agents, buffers, preservatives, perfumes, dyestuffs, lower alkanols, and the like.

If desired, further active ingredients may be incorporated in the compositions, e.g. antiinflammatory agents, antibacterials, antifungals, disinfectants, vitamins, sunscreens, antibiotics, or other anti-acne agents.

Examples of oils comprise fats and oils such as olive oil and hydrogenated oils; waxes such as beeswax and lanolin; hydrocarbons such as liquid paraffin, ceresin, and squalane; fatty acids such as stearic acid and oleic acid; alcohols such as cetyl alcohol, stearyl alcohol, lanolin alcohol, and hexadecanol; and esters such as isopropyl myristate, isopropyl palmitate and butyl stearate. As examples of surfactants there may be cited anionic surfactants such as sodium stearate, sodium cetylsulfate, polyoxyethylene laurylether phosphate, sodium N-acyl glutamate; cationic surfactants such as stearyldimethylbenzylammonium chloride and stearyltrimethylammonium chloride; amphophilic surfactants such as alkylaminoethylglycine hydrochloride solutions and lecithin; and nonionic surfactants such as glycerin monostearate, sorbitan monostearate, sucrose fatty acid esters, propylene glycol monostearate, polyoxyethylene oleylether, polyethylene glycol monostearate, polyoxyethylene sorbitan monopalmitate, polyoxyethylene coconut fatty acid monoethanolamide, polyoxyethylene polyoxypropylene glycol (e.g. the materials sold under the trademark "Pluronic"), polyoxyethylene castor oil, and polyoxyethylene lanolin. Examples of humectants include glycerin, 1,3-butylene glycol, and propylene glycol; examples of lower alcohols include ethanol and isopropanol; examples of thickening agents include xanthan gum, hydroxypropyl cellulose, hydroxypropyl methyl cellulose, polyethylene glycol and sodium carboxymethyl cellulose; examples of lipid absorbents comprise kaolin, bentonite and the like; examples of antioxidants comprise butylated hydroxytoluene, butylated hydroxyanisole, propyl gallate, citric acid and ethoxyquin; examples of chelating agents include disodium edetate and ethanehydroxy diphosphate; examples of buffers comprise citric acid, sodium citrate, boric acid, borax, and disodium hydrogen phosphate; and examples of preservatives are methyl parahydroxybenzoate, ethyl parahydroxybenzoate, dehydroacetic acid, salicylic acid and benzoic acid.

For preparing ointments, creams, toilet waters, skin milks, and the like, typically from 0.1 to 10% in particular from 0.1 to 5% and more in particular from 0.2 to 2.5% of the active ingredient ketoconazole optionally in an acid addition form, is combined in intimate admixture with a skin-acceptable carrier. For the ease of preparing high-quality compositions finely divided particles, preferably micronized particles of the active ingredient ketoconazole and optionally of other solid components, are employed. In ointments or creams, the carrier for example consists of 1 to 20%, in particular 5 to 15% of a humectant, 0.1 to 10% in particular from 0.5 to 5% of a thickener and water, or said carrier may consist of 70 to 99%, in particular 20 to 95% of a surfactant, and 0 to 20%, in particular 2.5 to 15% of a fat; or 80 to 99.9% in particular 90 to 99% of a thickener; or 5 to 15% of a surfactant, 2–15% of a humectant, 0 to 80% of an oil, very small (<2%) amounts of preservative, colouring agent and/or perfume, and water. In a toilet water, the carrier for example consists of 2 to 10% of a lower alcohol, 0.1 to 10% or in particular 0.5 to 1% of a surfactant, 1 to 20%, in particular 3 to 7% of a humectant, 0 to 5% of a buffer, water and small amounts (<2%) of preservative, dyestuff and/or perfume. In a skin milk, the carrier typically consists of 10–50% of oil, 1 to 10% of surfactant, 50–80% of water and 0 to 3% of preservative and/or perfume. Other active ingredients may be incorporated at doses ranging from 0.005% to 0.5%, particularly from 0.01% to 0.1%. In the aforementioned preparations, all % symbols refer to weight by weight percentage. The humectant, surfactant, oil, other active ingredient, etc. referred to in said preparations may be any such component used in the pharmaceutical or cosmetic arts but preferably will be one or more of the components mentioned hereinabove. Further, when in the above compositions one or more of the components make up the major part of the composition, the other ingredients can evidently be not present at their indicated maximum concentration and therefore will make up the remainder of the composition.

Besides the use of ketoconazole alone for topical treatment of acne, hyperkeratotic dermatoses and photo-aging of the skin, the present invention especially relates to pharmaceutical and cosmetic compositions as described above, in a novel combination with an appropriate retinoid and the use of said novel combination for the topical treatment of subjects affected by the above-mentioned dermatological conditions. Appropriate retinoids are, for example, all-trans retinoic acid (tretinoin) and 13-cis retinoic acid (isotretinoin). The effective amount of retinoid which can be incorporated in the above compositions comprising ketoconazole, ranges from 0.005% to 0.5% and preferably from 0.01% to 0.1% by weight. Preferably, the compositions comprising ketoconazole and a retinoid are applied as a single mixture of the two active ingredients. However, the active ingredients may also be applied in separate compositions. In this latter case, the composition comprising ketoconazole may be administered before, during or after the administration of the composition comprising the retinoid. In the aforementioned combination, each active ingredient may potentiate the activity of the other.

Interesting compositions among the groups of compositions described hereinbefore and -after, are those comprising a cyclodextrin (CD) or an ether derivative thereof, as a complexant and/or solubilizer. As examples of such cyclodextrins there may be mentioned α-CD, β-CD, γ-CD, and ether or mixed ether derivatives thereof. Particular such cyclodextrin derivatives are described in U.S. Pat. No. 3,459,731, EP-A-0,149,197 and EP-A-0,197,571.

Typically such ether or mixed ether derivatives comprise α, β- or γ-CD wherein one or more hydroxylgroups are substituted with $C_{1-6}$alkyl, particularly methyl, ethyl or isopropyl; hydroxy$C_{1-6}$alkyl, particularly hydroxyethyl, hydroxypropyl or hydroxybutyl; carboxy$C_{1-6}$alkyl, particularly carboxymethyl or carboxyethyl; or $C_{1-6}$alkyloxycarbonyl$C_{1-6}$alkyl. Especially noteworthy as complexants and/or solubilizers are β-CD, 2,6-dimethyl-β-CD and in particular 2-hydroxypropyl-β-CD, 2-hydroxyethyl-β-CD, 2-hydroxyethyl-γ-CD and 2-hydroxypropyl-γ-CD. In the aforementioned cyclodextrin derivatives, the DS (degree of substitution, i.e. the average number of substituted hydroxy functions per glucose unit) preferably is in the range of 0.125 to 3, in particular 0.3 to 2, more in particular 0.3 to 1 and the MS (molar degree of substitution, i.e. the average number of moles of the substituting agent per glucose unit) is in the range of 0.125 to 10, in particular of 0.3 to 3 and more in particular 0.3 to 1.5, preferably 0.35 to 0.50. Said compositions may conveniently be prepared by dissolving the cyclodextrin or ether derivative thereof in water and adding thereto ketoconazole as well as other adjuvants and components such as, for example, sodium chloride, potassium nitrate, glucose, mannitol, sorbitol, xylitol and buffers such as, for example, phosphate, acetate or citrate buffers; and optionally concentrating or drying the solution by evaporation under reduced pressure or by lyophilization. The amount of the cyclodextrin or ether derivative thereof in the final composition generally ranges from about 1% to about 40%, particularly form 2.5% to 25% and more particularly from 5 % to 20%.

Particularly interesting novel compositions are those described hereinabove comprising as active ingredients ketoconazole and a retinoic and which further comprise a cyclodextrin or an ether derivative thereof as a complexant and/or solubilizer. A main advantage of these compositions resides in the fact that the particularly labile retinoid, e.g. all-trans retinoic acid, is stabilized by the cyclodextrin or an ether derivative thereof. As a result the remaineance of the retinoid in the skin is improved and its effective concentration in the composition may be lowered, thereby significantly reducing irritation and peeling of the skin, which can be major side effects of treatment with too high a concentration of retinoid. In these preferred compositions the amount of ketoconazole ranges from 0.5% to 5%, particularly from 1% to 2%, the amount of retinoid from 0.005% to 0.5%, particularly from 0.01% to 0.1% and the amount of cycledextrin or ether derivative thereof from 5% to 25%, more particularly from 10% to 20% by weight.

Other particular compositions for use in the methods of the present invention are those wherein the active ingredient ketoconazole is formulated in liposome-containing compositions. Liposomes are artificial vesicles formed by amphophilic molecules such as polar lipids, for example, phosphatidyl cholines, ethanolamines and serines, sphingomyelins, cardiolipins, plasmalogens, phosphatidic acids and cerebiosides. Liposomes are formed when suitable amphophilic molecules are allowed to swell in water or aqueous solutions to form liquid crystals usually of multilayer structure comprised of many bilayers separated from each other by aqueous material (also referred to as coarse liposomes). Another type of liposome known to be consisting of a single bilayer encapsulating aqueous material is referred to as a unilamellar vesicle. If water-soluble materials are included in the aqueous phase during the swelling of the lipids they become entrapped in the aqueous layer between the lipid bilayers. Water-soluble active ingredients such as, for example, most of the salt forms of the compound ketoconazole are encapsulated in the aqueous spaces between the molecular layers. The lipid soluble active ingredient ketoconazole is predominantly incorporated into the lipid layers, although polar head groups may protrude from the layer into the aqueous space. The encapsulation of these compounds can be achieved by a number of methods. The method most commonly used involves casting a thin film of phospholipid onto the walls of a flask by evaporation from an organic solvent. When this film is dispersed in a suitable aqueous medium, multilamellar liposomes are formed. Upon suitable sonication, the coarse liposomes form smaller similarly closed vesicles.

Water-soluble active ingredients are usually incorporated by dispersing the cast film with an aqueous solution of the compound. The unencapsulated compound is then removed by centrifugation, chromatography, dialysis or other anknown suitable procedures. The lipid-soluble active ingredient is usually incorporated by dissolving it in the organic solvent with the phospholipid prior to casting the film. If the solubility of the material in the lipid phase is not exceeded or the mount present is not in excess of that which can be bound to the lipid, liposomes prepared by the above method usually contain most of the material bound in the lipid bilayers; separation of the liposomes from unencapsulated material is not required.

A particularly convenient method for preparing liposome formulated forms of the active ingredient ketoconazole is the method described in EP-0,253,619, incorporated herein by reference. In this method, single bilayered liposomes containing encapsulated active ingredients are prepared by dissolving the lipid component in an organic medium, injecting the organic solution of the lipid component under pressure into an aqueous component while simultaneously mixing the organic and aqueous components with a high speed homogenizer or mixing means, whereupon the liposomes are formed spontaneously.

The single bilayered liposomes containing the encapsulated active ingredient ketoconazole can be employed directly or they can be employed in a suitable pharmaceutically acceptable carrier for topical administration. The viscosity of the liposomes can be increased by the addition of one or more suitable thickening agents such as, for example xanthan gum, hydroxypropyl cellulose, hydroxypropyl methylcellulose and mixtures thereof. The aqueous component may consist of water alone or it may contain electrolytes, buffered systems and other ingredients, such as, for example, preservatives. Suitable electrolytes which can be employed include metal salts such as alkali metal and alkaline earth metal salts. The preferred metal salts are calcium chloride, sodium chloride and potassium chloride. The concentration of the electrolyte may vary from zero to 260 mM, preferably from 5 mM to 160 mM. The aqueous component is placed in a suitable vessel which can be adapted to effect homogenization by effecting great turbulence during the injection of the organic component. Homogenization of the two components can be accomplished within the vessel, or, alternatively, the aqueous and organic components may be injected separately into a mixing means which is located outside the vessel. In the latter case, the liposomes are formed in the mixing means and then transferred to another vessel for collection purpose.

The organic component consists of a suitable non-toxic, pharmaceutically acceptable solvent such as, for example ethanol, glycerol, propylene glycol and polyethylene glycol, and a suitable phospholipid which is soluble in the solvent. Suitable phospholipids which can be employed include lecithin, phosphatidylcholine, phosphatidylethanolamine, phosphatydylserine, phosphatidylinositol, lysophosphatidylcholine and phosphatidyl glycerol, for example. Other lipophilic additives may be employed in order to selectively modify the characteristics of the liposomes. Examples of such other additives include stearylamine, phosphatidic add, tocopherol, cholesterol and lanolin extracts.

It may be advantageous to use micronized forms of the active ingredient ketoconazole, i.e., material having an average particle size of less than 10 microns, as the high surface area will facilitate the dissolution of the liposomal components.

In addition, other ingredients which can prevent oxidation of the phospholipids may be added to the organic component. Examples of such other ingredients include tocopherol, butylated hydroxyanisole, butylated hydroxytoluene, ascorbyl palmitate and ascorbyl oleate. Preservatives such as benzoic acid, methyl paraben and propyl paraben may also be added.

The liposome-formulated forms of the active ingredient ketoconazole, particularly those obtained in the above-referred method of preparing such liposome formulated forms, may be used as such or in combination with any of the aforementioned careers to prepare ointments, creams, gelées, toilet waters, etc.

Apart from the above-described compositions, use may be made of covers, e.g. plasters, bandages, dressings, gauze pads and the like, containing an appropriate amount of a composition as referred hereinabove. In some cases use may be made of plasters, bandages, dressings, gauze pads and the like which have been impregnated or sprinkled with a liquid formulation containing the active agent, e.g. with an aseptic aqueous solution, or strewn with a powdery solid composition, or smeared, covered or coated with a semi-liquid composition.

The active ingredient ketoconazole may also be applicated by iontophoresis or by local injection, e.g. syringe or dermojet. In the latter modes of application the compositions conveniently will be in a liquid form. For applications based on iontophoresis use will be made of liquid formulations containing acid addition salts of the active ingredient ketoconazole.

The above described compositions containing ketoconazole are particularly useful for treating subjects suffering from acne, hyperkeratotic diseases and photo-aging of the skin and generally improve the quality of the skin, in particular of the human facial skin. These compositions should preferably be non-irritating and as far as possible they should be odorless and non-toxic. For convenience in applying to the skin, the composition usually contain, besides water or an organic solvent, several of certain organic emollients, emulsifiers for the aqueous and/or non aqueous phases of the compositions, wetting agents, preservatives and agents that facilitate the penetration and remainence of the active agents in the skin.

The ketoconazole containing compositions are applied topically to the area to be treated at regular intervals, as needed, generally once or twice a day. The duration of the treatment will depend upon the nature, extent and severity of the condition to be treated as well as the frequency of application of the composition.

In a further aspect of the present invention there are provided products containing the compound ketoconazole and a retinoid as a combined preparation for simultaneous, separate or sequential use in the topical treatment of subjects affected by acne, hyperkeratotic diseases and photo-aging of the skin. Such products may comprise, for example, a kit comprising a container with a suitable composition containing ketoconazole, and another container containing a composition with a retinoid, more in particular a composition wherein said retinoid is combined with a cyclodextrin or other derivative thereof. These products have the advantage that the appropriate amounts of each component and the sequence and the timing of the administration thereof can easily be selected and adjusted according to the response of the patient.

The following examples are intended to illustrate the scope of the present invention in all its aspects, and not to limit it thereto.

EXAMPLES

A. Composition examples

Example 1

Ketoconazole 2% Cream

| ketoconazole | 20 mg |
|---|---|
| propylene glycol | 200 mg |
| stearyl alcohol | 75 mg |
| cetyl alcohol | 20 mg |
| sorbitan monostearate | 20 mg |
| polysorbate 60 | 15 mg |
| isopropyl myristate | 10 mg |
| sodium sulfite anhydrous | 2 mg |
| polysorbate 80 | 1 mg |
| purified water q.s. ad 1 g (i.e. | 637 mg) |

Stearyl alcohol, cetyl alcohol, sorbitan monostearate and isopropyl myristate are introduced into a doublewall jacketed vessel and heated until the mixture has completely molten. This mixture is added to a separately prepared mixture of purified water, propylene glycol and polysorbate 60 having a temperature of 70° to 75° C. while using a homogenizer for liquids. The resulting emulsion is allowed to cool to below 25° C. while continuously mixing. A solution of ketoconazole, polysorbate 80 and purified water and a solution of sodium sulfite anhydrous in purified water are next added to the emulsion while continuously mixing. The cream is homogenized and filed into suitable tubes.

Example 2

2% Topical Gel

| ketoconazole | 20 mg |
|---|---|
| hydroxypropyl β-cyclodextrine | 200 mg |
| propylene glycol | 50 mg |
| ethyl alcohol 95% (v/v) | 50 mg |
| carrageenan PJ | 10 mg |
| hydrochloric acid | q.s. until solution |
| sodium hydroxide | q.s. ad pH 6.0 |
| purified water | q.s. ad 1 g. |

Method of Preparation

To a solution of hydroxypropyl β-cyclodextrine in purified water is added ketoconazole while stirring. Hydrochloric acid is added until complete solution and then sodium hydroxide is added until pH 6.0. This solution is added to a dispersion of carrageenan PJ in propylene glycol while mixing. While mixing slowly the mixture is heated to 50° C. and allowed to cool to about 35° C. whereupon the ethyl alcohol is added. The rest of the purified water is added and the mixture is mixed until homogenous.

Example 3

2% Topical Cream

| ketoconazole | 20 mg |
|---|---|
| hydroxypropyl β-cyclodextrine | 200 mg |
| mineral oil | 100 mg |
| stearyl alcohol | 20 mg |
| cetyl alcohol | 20 mg |
| glycerol monostearate | 20 mg |
| glycerol | 50 mg |
| sorbate 60 | 15 mg |
| polysorbate 60 | 35 mg |
| hydrochloric acid | q.s. until solution |
| sodium hydroxide | q.s. ad pH 6.0 |
| purified water | q.s. ad 1 g. |

Method of Preparation

To a solution of hydroxypropyl β-cyclodextrine in purified water is added ketoconazole while stirring. Hydrochloric acid is added until complete solution and next sodium hydroxide is added until pH 6.0. While stirring, glycerol and polysorbate 60 are added and the mixture is heated to 70° C. The resulting mixture is added to a mixture of mineral oil, stearyl alcohol, cetyl alcohol, stearyl monostearate and sorbate 60 having a temperature of 70° C. while mixing slowly. After cooling down to below 25° C., the rest of the purified water is added and the mixture is mixed until homogenous.

Example 4

2% Liposome Formulation

| | |
|---|---|
| ketoconazole microfine | 2 g |
| phosphatidyl choline | 20 g |
| cholesterol | 5 g |
| ethyl alcohol | 10 g |
| methyl paraben | 0.2 g |
| propyl paraben | 0.02 g |
| disodium edetate | 0.15 g |
| sodium chloride | 0.3 g |
| hydroxypropylmethylcellulose | 1.5 g |
| purified water | ad 100 g |

Method of Preparation

A mixture of ketoconazole microfine, phosphatidyl choline, cholesterol and ethyl alcohol is stirred and heated at 55°–60° C. until complete solution and is added to a solution of methyl paraben, propyl paraben, disodium edetate and sodium chloride in purified water while homogenizing. Hydroxypropylmethylcellulose in purified water is added and the mixing is continued until swelling is complete.

Example 5

2% Liposome Formulation

| | |
|---|---|
| ketoconazole microfine | 2 g |
| phosphatidyl choline | 10 g |
| cholesterol | 1 g |
| ethyl alcohol | 7.5 g |
| hydroxypropylmethylcellulose | 1.5 g |
| sodium hydroxide (1 N) | ad pH 5.0 |
| purified water | ad 100 g |

Method of Preparation

A mixture of phosphatidyl choline and cholesterol in ethyl alcohol is stirred and heated at 40° C. until complete solution. Ketoconazole microfine is dissolved in purified water by mixing while heating at 40° C. The alcoholic solution is added slowly to the aqueous solution while homogenizing during 10 minutes. Hydroxypropylmethylcellulose in purified water is added while mixing until swelling is complete. The resulting solution is adjusted to pH 5.0 with sodium hydroxide 1N and diluted with the rest of the purified water.

B. Clinical Examples

The useful acne reducing or curing properties of the compound ketoconazole to be used in the method of the present invention can be demonstrated by the following experiment.

Example 6

In a double-blind placebo controlled study patients with facial acne vulgaris were asked to apply a gel containing the active ingredient ketoconazole or placebo on small areas of the face with acne lesions. Ketoconazole was provided in 30 g robes containing 2% ketoconazole in a gel formulation. This formulation provided rapid penetration of the active ingredient into the skim. The gel had to be applied twice a day (morning and evening) immediately after cleaning the skin with fresh water. The gel was to be rubbed in gently without causing trauma to the skin and patients were told not press out any acne lesions in the face. Patients were observed at the start and every two weeks for a maximum of 8 weeks. During each visit the following signs and symptoms were evaluated and scored: papules, pustules, nodules, cysts, closed comedones, open comedones, inflammation and skin tension. The following table shows the end-results obtained during the clinical study as the global evaluation given by both the investigator and the patient after 8 weeks of treatment.

TABLE 1

| | By Investigator | | By Patient | |
|---|---|---|---|---|
| | 2% Ketoconazole (b.i.d.) | Placebo (b.i.d.) | 2% Ketoconazole (b.i.d.) | Placebo (b.i.d.) |
| Excellent | 10 | 5 | 9 | 5 |
| Good | 10 | 12 | 10 | 9 |
| Moderate | 1 | 2 | 3 | 5 |
| Weak | 3 | 5 | 2 | 4 |
| Poor | 1 | 6 | 1 | 7 |
| Total | 25 | 30 | 25 | 30 |
| p-value | p = 0.0208 Mann-Whitney U-test | | p = 0.0148 Mann-Whitney U-test | |

Example 7

In a comparative placebo controlled study the effect of ketoconazole (2%) and ketoconazole (2%)+all-trans retinoic acid (0.01%) was tested in patients with juvenile acne. The study was performed following the protocol described in the previous example and the interim results obtained during the clinical study are shown in Table 2.

TABLE 2

| | Placebo (b.i.d.) | Ketoconazole (2%, b.i.d.) | Ketoconazole (2%) + all-trans retinoic acid (0.01%, b.i.d.) |
|---|---|---|---|
| Number of patients | 51 | 26 | 14 |
| Score: | | | |
| excellent to good | 51% | 69% | 79% |
| moderate | 14% | 8% | 21% |
| weak to poor | 35% | 23% | 0% |
| % change in inflammation | −34% | −60% | −57% |
| Mean time to improvement (days) | 25 | 35 | 30 |
| End appreciation: | | | |
| better | 37% | 85% | 77% |
| worse | 34% | 15% | 0% |
| | | | 0.05 < p < 0.1 Mann-Whitney U-test |

I claim:

1. A composition for treating acne, hyperkeratotic dermatoses, and photo-aging of the skin, consisting essentially of a skin acceptable carrier; from 5% to 25% by weight of a cyclodextrin or an ether derivative thereof; and as the sole pharmaceutically active ingredients, from 0.5% to 5% by weight of ketoconazole and from 0.005% to 0.5% by weight of a retinoid.

2. The composition according to claim 1 consisting essentially of a skin acceptable carrier; from 1% to 2% by weight of ketoconazole; from 0.01% to 0.1% by weight of a retinoid; and from 10% to 20% by weight of a cyclodextrin or an ether derivative thereof.

3. The composition according to claim 2 wherein the cyclodextrin ether derivative is selected from the group consisting of 2-hydroxypropyl-β-cyclodextrin, 2-hydroxyethyl-β-cyclodextrin, 2-hydroxypropyl-γ-cyclodextrin, and 2-hydroxyethyl-γ-cyclodextrin.

4. The composition according to claim 3 wherein the molar degree of substitution in the cyclodextrin ether derivative ranges from 0.35 to 0.5.

5. The composition according to claim 4 wherein the retinoid is selected from the group consisting of all-trans retinoic acid (tretinoin) and 13-cis retinoic acid (isotretinoin).

6. A method of topically treating acne, hyperkeratotic dermatoses or photo-aging of the skin in a patient suffering therefrom, which comprises administering to the affected site on the skin of the patient an effective amount of a composition consisting essentially of a skin acceptable carrier; from 5% to 25% by weight of a cyclodextrin or an ether derivative thereof; and as the sole pharmaceutically active ingredients, from 0.5% to 5% by weight of ketoconazole and from 0.005% to 0.5% by weight of a retinoid.

7. The method according to claim 6 wherein the composition consists essentially of a skin acceptable carrier; from 1% to 2% by weight of ketoconazole; from 0.01% to 0.1% by weight of a retinoid; and from 10% to 20% by weight of a cyclodextrin or an ether derivative thereof.

8. The method according to claim 7 wherein the cyclodextrin ether derivative is selected from the group consisting of 2-hydroxypropyl-β-cyclodextrin, 2-hydroxyethyl-β-cyclodextrin, 2-hydroxypropyl-γ-cyclodextrin, and 2-hydroxyethyl-γ-cyclodextrin.

9. The method according to claim 8 wherein the molar degree of substitution in the cyclodextrin ether derivative ranges from 0.35 to 0.5.

10. The method according to claim 9 wherein the retinoid is selected from the group consisting of all-trans retinoic acid (tretinoin) and 13-cis retinoic acid (isotretinoin).

11. A composition for treating acne, hyperkeratotic dermatoses, and photo-aging of the skin, consisting essentially of a skin acceptable carrier; from 5% to 25% by weight of a cyclodextrin or an ether derivative thereof; and as the sole pharmaceutically active ingredients, from 0.5% to 5% by weight of ketoconazole and an effective amount of a retinoid.

12. A method of topically treating acne, hyperkeratotic dermatoses, or photo-aging of the skin in a patient suffering therefrom, which comprises administering to the affected site on the skin of the patient an effective amount of the composition of claim 11.

* * * * *